United States Patent [19]

Sandhu et al.

[11] Patent Number: 5,036,015
[45] Date of Patent: Jul. 30, 1991

[54] METHOD OF ENDPOINT DETECTION DURING CHEMICAL/MECHANICAL PLANARIZATION OF SEMICONDUCTOR WAFERS

[75] Inventors: Gurtej S. Sandhu; Laurence D. Schultz; Trung T. Doan, all of Boise, Id.

[73] Assignee: Micron Technology, Inc., Boise, Id.

[21] Appl. No.: 586,996

[22] Filed: Sep. 24, 1990

[51] Int. Cl.$^5$ .................................. H01L 21/66
[52] U.S. Cl. ............................. 437/8; 437/225; 156/645; 156/626; 51/283 R; 51/165 R
[58] Field of Search ............... 437/8, 225, 7; 156/645, 156/627, 654, 626; 51/165 R, 283 R

[56] References Cited

U.S. PATENT DOCUMENTS

| | | | |
|---|---|---|---|
| 3,699,722 | 10/1972 | Davidson et al. | 51/283 |
| 3,841,031 | 10/1974 | Walsh | 51/283 |
| 3,979,239 | 9/1976 | Walsh | 437/225 |
| 4,193,226 | 3/1980 | Gill, Jr. et al. | 51/124 R |
| 4,358,338 | 11/1982 | Downey et al. | 156/627 |
| 4,663,890 | 5/1987 | Brandt | 51/283 R |
| 4,793,895 | 12/1988 | Kaanta et al. | 156/645 |
| 4,811,522 | 3/1989 | Gill, Jr. | 51/131.1 |
| 4,879,258 | 11/1989 | Fisher | 437/225 |
| 4,910,155 | 3/1990 | Cote et al. | 437/225 |
| 4,956,313 | 9/1990 | Cote et al. | 156/645 |

Primary Examiner—Brian E. Hearn
Assistant Examiner—Michael Trinh
Attorney, Agent, or Firm—Stephen A. Gratton; Robert A. de Groot

[57] ABSTRACT

A method and apparatus for detecting a planar endpoint on a semiconductor wafer during chemical/mechanical planarization of the wafer. The planar endpoint is detected by sensing a change in friction between the wafer and a polishing surface. This change of friction may be produced when, for instance, an oxide coating of the wafer is removed and a harder material is contracted by the polishing surface. In a preferred form of the invention, the change in friction is detected by rotating the wafer and polishing surface with electric motors and measuring current changes on one or both of the motors. This current change can then be used to produce a signal to operate control means for adjusting or stopping the process.

11 Claims, 2 Drawing Sheets

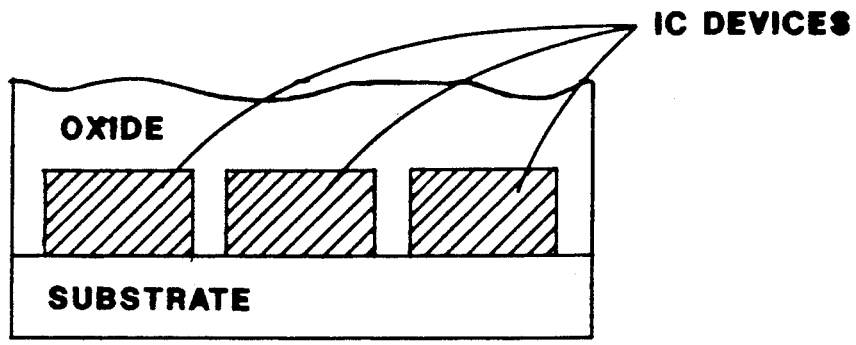
FIGURE 1 (PRIOR ART)
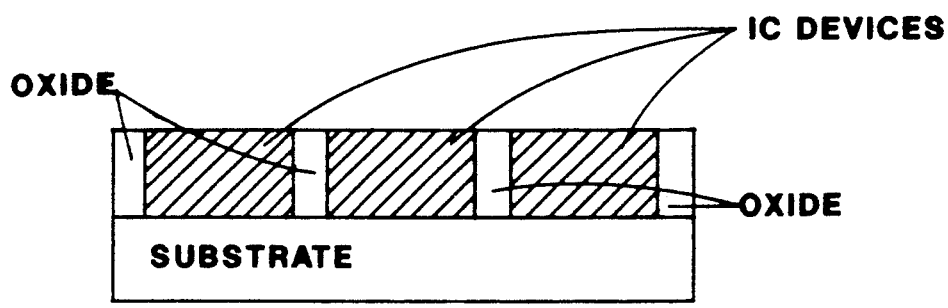
FIGURE 2 (PRIOR ART)
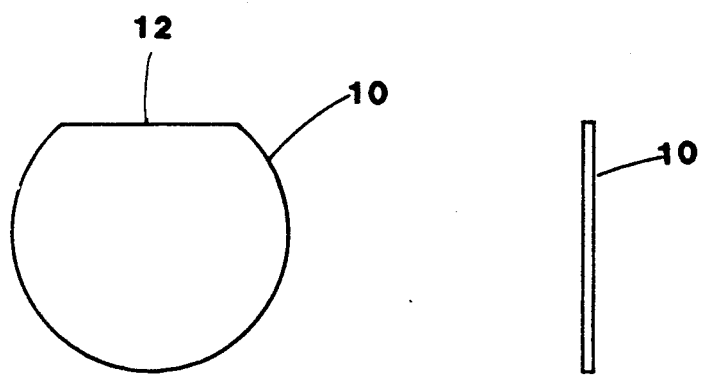
FIGURE 3
(PRIOR ART)
FIGURE 4
(PRIOR ART)

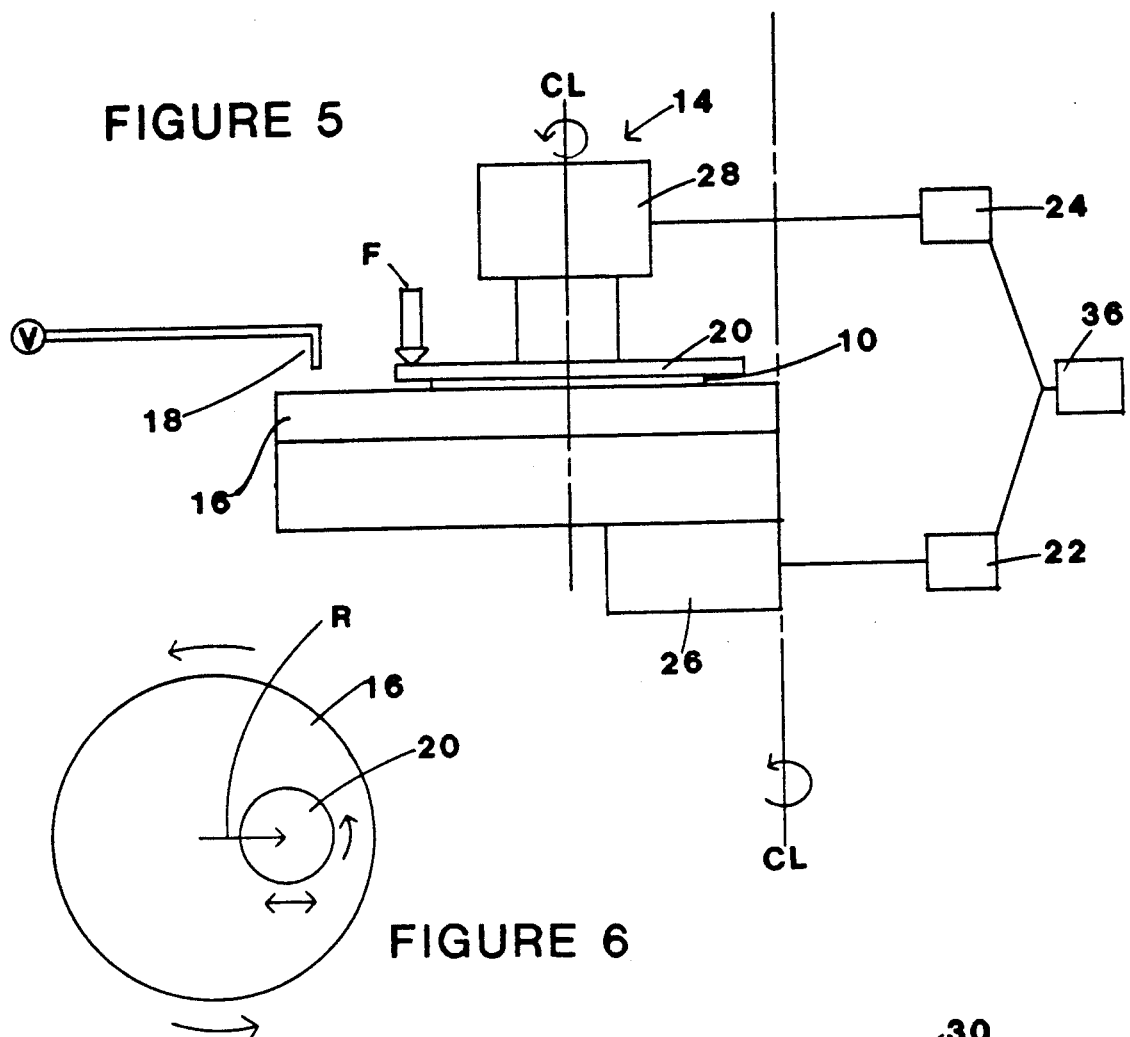
FIGURE 5
FIGURE 6
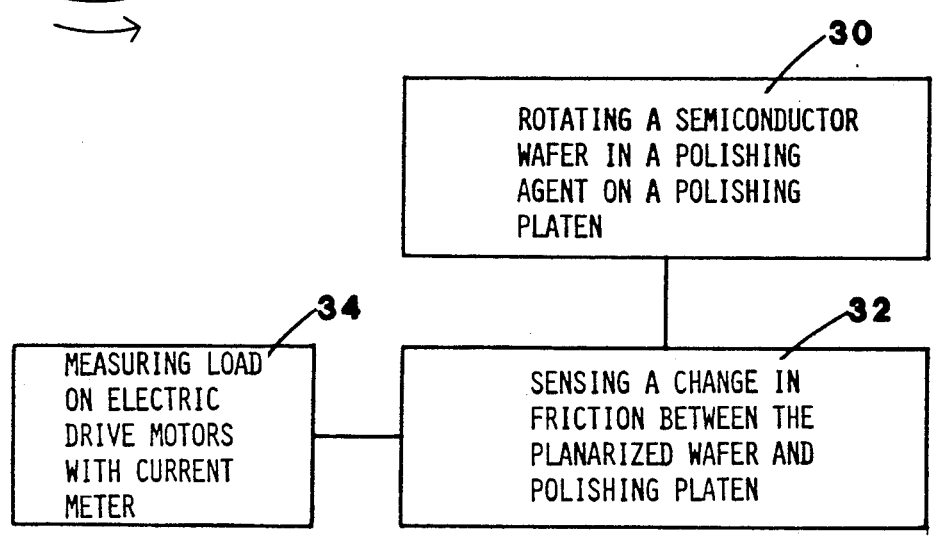
FIGURE 7

METHOD OF ENDPOINT DETECTION DURING CHEMICAL/MECHANICAL PLANARIZATION OF SEMICONDUCTOR WAFERS

FIELD OF THE INVENTION

This invention relates to semiconductor manufacture and, more particularly, to a novel method and apparatus for detecting a planar endpoint in a semiconductor wafer during mechanical planarization.

BACKGROUND OF THE INVENTION

In semiconductor manufacture, extremely small electronic devices are formed in separate dies on a thin, flat semiconductor wafer. In general, various materials which are either conductive, insulating, or semiconducting are utilized to form a semiconductor wafer. These materials are patterned, doped with impurities, or deposited in layers by various processes to form the integrated circuits. A completed device is referred to as a semiconductor.

One process that is utilized in the manufacture of semiconductors is referred to as chemical mechanical planarization (CMP). In general, chemical mechanical planarization involves holding or rotating a thin, flat wafer of semiconductor material against a wetted polishing surface under controlled chemical, pressure, and temperature conditions. A chemical slurry containing a polishing agent such as alumina or silica is utilized as the abrasive medium. Additionally, the chemical slurry may contain chemical etches for etching various surfaces of the wafer.

In general, a semiconductor wafer is subjected to chemical mechanical planarization to remove topography, layers of material, surface defects such as crystal lattice damage, scratches, roughness, or embedded particles of dirt or dust. This process is utilized in the formation of various integrated circuit devices of a semiconductor and to improve the quality and reliability of a semiconductor.

In the mechanical planarization process, a rotating polishing head is typically utilized to hold the wafer under controlled pressure against a rotating polishing platen. The polishing platen is typically covered with a relatively soft, wetted material such as blown polyurethane. The chemical slurry is metered onto the polishing platen and is selected to provide an abrasive medium and chemical activity for the etching.

Such apparatus for polishing thin, flat semiconductor wafers are well known in the art. U.S. Pat. Nos. 4,193,226 and 4,811,522 to Gill, Jr. and U.S. Pat. No. 3,841,031 to Walsh, for instance, disclose such apparatus. Another such apparatus is manufactured by Westech Engineering and designated as a Model 372 Polisher.

A particular problem encountered in the use of such chemical mechanical polishing apparatus is in the determination that a part has been planed to a desired planar endpoint. It is often desirable, for example, to remove a thickness of oxide material which has been deposited onto a substrate, and on which a variety of integrated circuit devices have been formed. In removing or planarizing this oxide, it is desirable to remove the oxide to the top of the various integrated circuit devices without removing any portion of a device.

In the past, this planarization process has been accomplished by control of the rotational speed, downward pressure, chemical slurry, and time of the planarization process. The planar endpoint of a planarized surface has been detected by mechanically removing the semiconductor wafer from the planarization apparatus and physically measuring the semiconductor wafer by techniques which ascertain dimensional and planar characteristics. If the semiconductor wafer does not meet specification, it must be loaded back into the planarization apparatus and planarized again. Alternately, an excess of material may have been removed from the semiconductor wafer rendering the part as substandard.

In general, however, there has been no provision in the art for in situ endpoint detection of a planarized surface during the planarization process. The present invention is directed to a novel method and apparatus for in situ endpoint detection of a planarized surface during the mechanical planarization process.

SUMMARY OF THE INVENTION

In accordance with the present invention, a novel method and apparatus for endpoint detection of a planarized surface of a semiconductor wafer during mechanical planarization of the wafer is provided. In general, the method and apparatus of the invention senses a change of friction between the wafer and a polishing surface to detect the endpoint of a planarized surface. A change in friction occurs when, for example, a first material or film of the wafer is removed and a planar surface of the wafer formed of a different material or film is exposed. An oxide or nitride coating, for instance, may be removed to expose polysilicon or a base metallic film.

The method of the invention, generally stated, comprises:

rotating a semiconductor wafer against a rotating polishing platen in a polishing slurry; and sensing a change in friction between the planarized wafer surface and the polishing platen in order to detect a planar endpoint of the wafer.

Apparatus for planarizing a semiconductor wafer in accordance with the method of the invention comprises:

holding means in the form of a rotatable polishing head for holding a semiconductor wafer;

polishing means including a rotatable polishing platen and a polishing slurry for the contacting and planarizing the topography of the wafer; and sensing means for sensing a change in the coefficient of friction between the surface of the wafer and the polishing platen.

In a preferred form of the invention, the polishing platen and polishing head are both rotated by electric drive motors. The sensing means comprises a current meter which senses a change in motor current of either or both drive motors during the planarization process. This load change can then be equated to a change in the coefficient of friction between the surface of the wafer and the polishing platen.

Other objects, advantages, and capabilities of the present invention will become more apparent as the description proceeds.

BRIEF DESCRIPTION OF THE DRAWINGS

FIG. 1 is an enlarged side elevation view of a portion of a semiconductor wafer prior to mechanical planarization;

FIG. 2 is an enlarged side elevation view of a portion of a semiconductor wafer after mechanical planarization;

FIG. 3 is a plan view of a semiconductor wafer;

FIG. 4 is a side elevation view of FIG. 3;

FIG. 5 is a schematic view of mechanical planarization apparatus having endpoint detection apparatus constructed in accordance with the invention;

FIG. 6 is a schematic plan view showing rotation of a polishing platen and polishing head for mechanical planarization of a semiconductor wafer; and FIG. 7 is a block diagram of a method of endpoint detection in accordance with the invention during mechanical planarization of a semiconductor wafer.

DETAILED DESCRIPTION OF THE PREFERRED EMBODIMENT

Referring now to FIG. 1, a portion of a semiconductor wafer is shown prior to mechanical planarization of the semiconductor wafer. A semiconductor wafer typically includes a substrate on which a plurality of micro devices have been formed. The wafer substrate is typically formed of a single crystal silicon material. The micro devices are formed by patterning regions on the substrate and patterning layers on the substrate. A chemical mechanical planarization process may be utilized, for instance, to remove a portion of a layer. Different layers are generally formed of different materials. During formation regions or vias on the silicon substrate may be patterned for contact with a plurality of IC devices as shown in FIG. 1. An insulating or oxide coating may then be formed or deposited on the substrate and over the IC devices. As shown in FIG. 2, it may be necessary to remove the oxide coating to the level of the IC devices to form insulating spacers therebetween. This can be accomplished by a chemical mechanical planarization process.

In general, a chemical mechanical planarization process involves mechanically polishing a thin, flat semiconductor wafer under controlled pressure, temperature, time, and chemical conditions. Such a semiconductor wafer is shown in FIGS. 3 and 4 and is generally designated as 10. As shown, the wafer is generally circular in shape and includes a major flat 12. The size of the wafer 10 is typically about 5 inches in diameter but may be several inches smaller or longer. A plurality of patterned dies (not shown) are formed on the surface of the wafer, each having a micro topography. The micro topography of each patterned die can be altered as illustrated by the example of FIGS. 1 and 2 by the mechanical planarization process. Alternately, mechanical planarization can be utilized to form other wafer topography and in the polishing, cleaning, and planing of the wafer surface.

In general, different layers of the semiconductor wafer are formed of different materials (i.e. metallic film, polysilicon film, insulators) which have a different relative hardness. The IC devices formed in FIGS. 1 and 2, for instance, are generally harder than the oxide coating formed thereon. In general, the method and apparatus of the invention utilizes this relative difference between materials to detect planar endpoints during the mechanical planarization process.

Referring now to FIG. 5, a mechanical planarization apparatus constructed with endpoint detection apparatus in accordance with the invention is shown and generally designated as 14. The mechanical planarization apparatus 14 includes:

polishing means in the form of a rotatable polishing platen 16 and a polishing agent 18 which is applied to the surface of the polishing platen 16;

holding means for holding the semiconductor wafer 10 in the form of a rotatable polishing head 20 mounted for holding and rotating the wafer 10 against the polishing platen 16 under a controlled force F; and endpoint detection means in the form of motor current meters 22,24 which measure the load or amperage on electric drive motors 26,28 for the polishing platen 16 and polishing head 20 and sense a change in friction between the wafer 10 and the polishing platen 16.

As shown in FIG. 5, the polishing head 20 holds the wafer 10 for rotation against the polishing platen 16 under a controlled force (F). A direction of rotation of the polishing platen 16 and polishing head 20 is preferably the same. This is shown in FIG. 6. (Alternately, the polishing platen 16 and polishing head 20 may be rotated in opposite directions). Additionally, the polishing head 20 is constructed to move across the polishing platen 16 as indicated by the double headed arrow in FIG. 6. The polishing agent 18 is dispensed as shown in FIG. 5 through a suitable valved conduit onto the surface of the polishing platen 16. Such mechanical planarization apparatus are well known in the art. One such apparatus is manufactured by Westech Engineering and designated as a Model 372 Polisher.

In general, with such polishing apparatus, all functions (speed, force (F), temperature, slurry, chemical components) are under computer control. Additionally, the wafer size may be varied and an environment enclosure (not shown) may be provided to protect the surroundings from particles or contamination.

In general, the apparatus of the invention adds the current meters 22,24 to the drive motors 26,28 of the planarization apparatus of the prior art in order to detect the amperage or load on the motors 26,28. Such current meters 22,24 must necessarily be sensitive to small variations in current, but are commercially available in the art. In effect, the current meters 22,24 constantly monitor the force required to rotate the wafer 10 on the polishing platen 16. Any change in this force will signal the change in friction of the exposed surface of the wafer 10, which occurs at a planar endpoint.

The load or amperage draw of the motors 26,28 is a function of the force (F) exerted by the polishing head 20 and wafer 10 on the polishing platen 16. Additionally, the load is a function of the coefficient of friction between the wafer 10, polishing slurry 18, and polishing platen 16. A change in the coefficient of friction between these surfaces will change the load or amperage draw of the drive motors 26,28. If, for example, the oxide coating of a wafer 10, as shown in FIG. 1, is removed to the plane of the tops of the (IC) devices the change in coefficient of friction can be detected by a different amperage draw of the current meters 22,24. The point at which the coefficient of friction changes is thus equated to a planar endpoint of the wafer 10.

The current of either the polishing platen drive motor 26 or the polishing head drive motor 28 or both may be monitored. This change can be utilized to generate a signal from the current meters 22,24 to a control means 36 (FIG. 5), which stops or adjusts apparatus and the mechanical planarization process as required. As is apparent to those skilled in the art, such control means 36 could be formed by equipment and procedures known in the art and may include visual signals and manual controls.

The method of the invention is adapted to detect the endpoint of a planarized wafer surface in such an apparatus and can be summarized by the steps of:

rotating a semiconductor wafer 10 in a polishing agent 18 on a polishing platen 16, step 30; and sensing a change in friction between the surface of the wafer 10 and the polishing platen 16, step 32.

As previously explained, in a preferred form of the invention, sensing of a change in friction is accomplished by measuring the load on electric drive motors 26,28 with current meters 22,24, step 34. This change in friction between the surface of the wafer and the polishing platen 16 can then be equated to a planar endpoint of the wafer surface. This concept can be more fully explained with reference to FIGS. 1 and 2. As the semiconductor wafer 10 is rotated and pressed against the polishing platen 16, the oxide surface (FIG. 1) of the wafer 10 contacts the surface of the polishing platen 16. The oxide surface has a hardness which produces a certain coefficient of friction by contact with the surface of the polishing platen 16 and polishing agent 18. As previously stated, the surface of the polishing platen 16 may typically be formed of a relatively soft material such as blown polyurethane.

This coefficient of friction is generally constant until the oxide is polished away to the point in which the surface of the IC devices is exposed (FIG. 2). At this point, the IC devices contact the surface of the polishing platen 16. In general, the IC devices may be formed of a harder material than the oxide coating (for example, a metallic film may be contacted). A different coefficient of friction thus occurs between the surface of the wafer 10 and the surface of the polishing platen 16. Assuming the downward force F (FIG. 5) on the wafer 10 and the rotational speed of the polishing head 20 and polishing platen 16 remains constant, this different coefficient of friction will produce a different load on the electric drive motors 26,28. This load can be sensed by the current meters 22,24. A planar endpoint in which the oxide coating has been removed to the top of the IC devices is thus detected.

This change in coefficient of friction between the planar surfaces, although relatively small, is subjected to a multiplying factor if the current draw on the drive motor 26 for the polishing platen 16 is monitored. The multiplying factor can be determined as follows.

The electric drive motor 26 for the polishing platen 16 produces a torque (T) which is opposed by the rotating polishing head 10. This torque (T) is also related to the force (F) (FIG. 5) pressing the polishing head 20 against the polishing platen 16. As is apparent force (F) is also related to but is different than the coefficient of friction between the surface of the wafer 10, polishing slurry 18, and polishing platen 16. Additionally, the torque (T) is dependent on the distance "R" (FIG. 6) of the polishing head 20 from the center of rotation of the polishing platen 16. This well-known relationship can be expressed by the formula $T = F \times r$. A small change in the coefficient of friction between the surfaces can thus be detected as a change in the torque (T) seen by the electric drive motors 26 (and, thus, the current flow) multiplied by the radius (r).

Additionally, as is apparent, changes in the coefficient of friction on relatively larger diameter wafers are generally larger and thus easier to detect than on relatively smaller diameter wafers.

The invention thus provides a simple yet unobvious method and apparatus for detecting the planar endpoint of a semiconductor wafer during a mechanical planarization process. While the process of the invention has been described with reference to a preferred embodiment thereof, as will be apparent to those skilled in the art, certain changes and modifications can be made without departing from the scope of the invention as defined by the following claims.

What is claimed is:

1. A method for mechanically planarizing a semiconductor wafer comprising:
    a. holding the wafer in contact with a polishing platen in the presence of a chemical slurry;
    b. rotating the wafer with respect to and against the polishing platen; and
    c. sensing a change in friction between the wafer and the polishing platen to detect a planar endpoint on the wafer.

2. The process as claimed in claim 1 and further comprising:
    d. rotating the wafer or the polishing platen with an electric drive motor; and
    e. sensing a change in friction with a current meter for the drive motor which detects a change in amperage through the drive motor.

3. The process as claimed in claim 2 and wherein:
    sensing the planar endpoint occurs when an oxide coating on the wafer is planarized and a surface of the wafer including a different material is contacted by the polishing platen.

4. The process as claimed in claim 2 and wherein:
    the current meter measures a current flow to the drive motor which is equated to the torque output and to the current draw of the motor multiplied by a multiplying factor.

5. The process as claimed in claim 4 and wherein:
    torque (T) on the motor is equated to the force (F) between the wafer and polishing platen and to the radius (r) of the wafer from the center of the polishing platen by the formula: $T = F \times r$.

6. A method of detecting a planar endpoint on a semiconductor wafer during a mechanical planarization process comprising:
    a. rotating the wafer with respect to a polishing platen; and
    b. sensing a change in friction between the wafer and polishing platen to detect a planar endpoint on the wafer.

7. A method as recited in claim 6 and wherein:
    c. the wafer is rotated with respect to the polishing platen by an electric motor; and
    d. sensing a change in friction is accomplished by a current meter for the motor.

8. The method as recited in claim 7 and wherein:
    the planar endpoint occurs when coating on the wafer is removed to expose a surface formed with a different material.

9. The method as recited in claim 8 and wherein:
    both the wafer and polishing platen are rotated.

10. The method as recited in claim 9 and wherein:
    both the wafer and polishing platen are rotated.

11. The method as recited in claim 7 and wherein:
    the coefficient of friction between the wafer and polishing platen is equated to the torque (T) on the motor by the equation $T = F \times r$, where "F" is a function of the coefficient of friction and "r" is a radius from the center of the polishing platen to the center of the wafer.

* * * * *

Adverse Decision In Interference

Patent No. 5,036,015, Gurtej S. Sandhu, Laurence D. Schultz, Trung T. Doan, METHOD OF ENDPOINT DETECTION DURING CHEMICAL/MECHANICAL PLANARIZATION OF SEMICONDUCTOR WAFERS, Interference No. 103,957, final judgment adverse to the patentees rendered March 9, 2001, as to claims 1-11.

*(Official Gazette May 15, 2001)*